United States Patent
Saito et al.

(10) Patent No.: US 6,723,667 B1
(45) Date of Patent: Apr. 20, 2004

(54) PACK PREPARATION

(75) Inventors: Masato Saito, Odawara (JP); Akihiro Kuroda, Hiratsuka (JP); Yoshikuni Yamashita, Manazurumachi (JP)

(73) Assignee: Kanebo, Ltd., Tokyo (JP)

( * ) Notice: Subject to any disclaimer, the term of this patent is extended or adjusted under 35 U.S.C. 154(b) by 0 days.

(21) Appl. No.: 09/743,592

(22) PCT Filed: Jul. 13, 1998

(86) PCT No.: PCT/JP98/03119

§ 371 (c)(1),
(2), (4) Date: Mar. 19, 2001

(87) PCT Pub. No.: WO00/02526

PCT Pub. Date: Jan. 20, 2000

(51) Int. Cl.$^7$ ............... B32B 27/04; B32B 27/12; B32B 5/02

(52) U.S. Cl. ............... 442/123; 156/247; 424/402; 424/443; 424/447; 442/394; 442/396; 428/520; 428/522; 524/703

(58) Field of Search ............... 428/520, 522; 524/702; 442/123, 394, 396; 424/402, 443, 447; 156/247

(56) References Cited

U.S. PATENT DOCUMENTS 5,827,920 A * 10/1998 Watanabe et al. ............ 424/59
2002/0081321 A1 * 6/2002 Konno et al. ............ 424/401

FOREIGN PATENT DOCUMENTS

| JP | 04-095015 | 3/1992 |
|---|---|---|
| JP | 04-346911 | 12/1992 |
| JP | 05-043445 | 2/1993 |
| JP | 05-058870 | 3/1993 |
| JP | 05-139951 | 6/1993 |
| JP | 08-040882 | 2/1996 |
| JP | 08-169809 | 7/1996 |
| JP | 08-188527 | 7/1996 |
| JP | 10-046142 | 2/1998 |

* cited by examiner

Primary Examiner—D. Lawrence Tarazano
(74) Attorney, Agent, or Firm—Hogan & Hartson, LLP

(57) ABSTRACT

Disclosed is a pack comprising a water-soluble polymer and a Saxifrage extract. The pack of the present invention allays irritation and pain on peeling, firms up the skin after use, moisturizes the skin, and has excellent remoisturizing properties, quick-drying properties and facility.

18 Claims, No Drawings

PACK PREPARATION

TECHNICAL FIELD

The present invention relates to a pack and a sheet-like pack and, more particularly, to a pack and a sheet-like pack, which have an excellent effect of allaying irritation when the pack or sheet-like pack is peeled off from the skin, firming up the skin in or after use, and moisturizing the skin.

BACKGROUND ART

A main pack is a peel-off type pack containing polyvinyl alcohol or a vinyl acetate resin which has a film-forming capability. Recently, a sheet-like pack, which is prepared by drying a pack itself, or applying the pack on a nonwoven fabric or a film and drying the pack, thereby forming the pack into a thin film, has widely been used because of its quick-drying properties and facility.

The above pack can remove stain of the skin such as keratotic plug by applying the pack on the skin, drying the pack and peeling of f the dried pack from the skin after drying, or applying a sheet-like pack on the skin wetted with water or a beauty wash, drying and peeling off the sheet-like pack. However, we sometimes feel irritation and pain when the pack or sheet-like pack is peeled off from the skin. Although stain of the skin is removed, the effect of firming up the skin after use and moisturizing the skin can not be obtained. In the sheet-like pack, remoisturizing properties capable of easily exerting adhesion properties again by dissolving the pack using water or a beauty wash.

Thus, an object of the present invention is to provide a pack of the present invention allays irritation and pain on peeling, firms up the skin after use, moisturizes the skin, and has excellent remoisturizing properties, quick-drying properties and facility, or a sheet-like pack.

DISCLOSURE OF THE INVENTION

The present invention provides a pack comprising a water-soluble polymer and a Saxifrage extract, or a pack comprising a water-soluble polymer and a Saxifrage extract, said pack being formed into a sheet directly or on a substrate.

The present invention preferably provides a pack or sheet-like pack, comprising one or more water-soluble polymers selected from the group consisting of polyacrylic acid, polymethacrylic acid, and copolymers of acrylic acid and methacrylic acid, a Saxifrage extract and a perfume.

BEST MODE FOR CARRYING OUT THE INVENTION

The sheet-like pack of the present invention is obtained by directly drying a pack comprising a water-soluble polymer, a Saxifrage extract and a solvent such as water, or applying the pack on a substrate such as nonwoven fabric, paper, synthetic film or the like and removing the solvent to form a sheet-like laminate.

In the present invention, the water-soluble polymer is a polymer substance used to enhance the film-forming properties and examples thereof include polyacrylic acid, polyacrylate, polymethacrylic acid, polymethacrylate, polyvinyl alcohol, polyvinyl pyrrolidone, polyacrylamide, polyacrylamide salt, polymethacrylamide, polymethacrylamide salt, methacryloyloxyethyltrimethylammonium chloride, methacrylamidepropyltrimethylammonium chloride, N-n-botoxymethylacrylamide, N-iso-butoxyacrylamide, t-butylacrylamidesulfonic acid, t-butylacrylamidesulfonate, dimethylaminopropylmethacrylamide, or copolymers of these polymerizable monomer raw materials and other polymerizable monomers, or carboxymethylcellulose salt, alginate, carrageenan and xanthane gum. The amount of the water-soluble polymer is preferably within a range from 1.0 to 80% by weight based on the total weight of the pack. In case of the sheet-like pack, the water-soluble polymer is preferably incorporated so that the amount of the water-soluble polymer is within a range from 2.0 to 99.4% by weight in the pack excluding a substrate such as nonwoven fabric when the water content of the sheet-like pack after drying is within a range from 0.1 to 20% by weight.

Among the above water-soluble polymers, one or more water-polymerizable polymers selected from the group consisting of polyacrylic acid, polymethacrylic acid, and copolymers of acrylic acid and methacrylic acid are preferable because of excellent film-forming properties, remoisturizing properties and adhesion properties capable of removing stain of the skin. It is preferable to use one or more water-polymerizable polymers of polyacrylic acid, polymethacrylic acid, and copolymers of acrylic acid and methacrylic acid in combination with polyvinyl alcohol because of particularly excellent film-forming properties and adhesion properties capable of removing stain of the skin. The polyacrylic acid, polymethacrylic acid and copolymers thereof may be water-soluble polyacrylic acid polymers prepared by partially copolymerizing with the other polymerizable monomer, or water-soluble polyacrylate, water-soluble polymethacrylate and water-soluble acrylic acid-methacrylic acid copolymer which are prepared by partially neutralizing the polymer with sodium hydroxide, potassium hydroxide, triethaniolamine or the like.

The Saxifrage extract used in the present invention is prepared by extracting the unchopped leaf of Saxifrage (Saxifragastolonifera Meerb.) with purified water, ethanol, 1,3-butylene glycol or the like, and is an extract prepared by concentrating the extract solution or a powder prepared by drying the extract solution and pulverizing the dried extract. Saxifrage-has generally been used as a folk medicine for whooping cough and ear discharge of children, and Saxifrage is also used by applying it on swelling, burn, frostbite or the like after roasting.

In the present invention, use of the Saxifrage extract in combination with the perfume is preferable to remarkably exert the effect of allaying irritation or pain when the pack or sheet-like pack is peeled off, firming up the skin after use, moisturizing the skin, and exerting refreshing and relaxing effects due to the perfume. The perfume may be a compound perfume made of a natural perfume, a synthesis perfume or a combination thereof, but a perfume which is solid at normal temperature and a perfume capable of markedly remaining a faint scent are preferable because the perfume is not volatilized during the preparation of the sheet-like pack. Examples of the perfume include menthol, borneol, camphor, coumarin, indan, tetralin musk, macrocyclic musk, heliotropin and the like. Among these perfumes, preferable perfumes are borneol and camphor, which firm up the skin, refresh users and remarkably exert refreshing and relaxing effects, by using in combination with the Saxifrage extract.

The method of incorporating the above perfume into the pack or sheet-like pack includes, for example, a method of previously mixing the perfume with the pack, a method of directly forming the pack into a sheet by drying, a method of applying the pack on a substrate such as nonwoven fabric, paper, synthetic resin film or the like, and removing a solvent to form a sheet-like laminate, a method of perfuming a nonwoven fabric used in the sheet-like pack, or a method of removing the solvent to form a sheet-like laminate and spraying a perfume, thereby impregnating a sheet-like pack with the perfume.

The amount of the Saxifrage extract is preferably within a range from 0.001 to 5.0% by weight, calculated on the basis of the dry residue of the Saxifrage extract, based on the total weight of the pack. In case of the sheet-like pack, the Saxifrage extract is preferably incorporated into the pack excluding a substrate such as nonwoven fabric in the amount within a range from 0.01 to 10.0% by weight calculated on the basis of the dry residue of the Saxifrage extract when the water content of the sheet-like pack after drying is within a range from 0.1 to 30% by weight. Similarly, the amount of the perfume is preferably within a range from 0.0001 to 1.0% by weight based on the total weight of the pack. In case of the sheet-like pack, when the water content of the sheet-like pack after drying is within a range from 0.1 to 30% by weight, the perfume is preferably incorporated into the pack excluding a substrate such as nonwoven fabric in the amount within a range from 0.001 to 2.0% by weight.

In addition to the essential components described above, the respective components such as pigments, antiseptics, humectants, alcohols, dispersants and oil components can be incorporated into the pack or sheet-like pack of the present invention as far as the effect of the present invention is not adversely affected. It is preferable to incorporate pigments having an average primary particle diameter within a range from 0.01 to 1 $\mu$m (e.g. titanium oxide, silica, etc.) and humectants such as glycerin, 1,3-butylene glycol, diglycerin, propylene glycol, trimethylglycine, polyethylene glycol, sorbitol, etc. because the effect of removing stain from the skin and the effect of moisturizing the skin are enhanced.

The pack of the present invention is prepared by dissolving or dispersing the above components in a solvent such as water using a conventional method, the amount of water to be added being within a range from 7 to 70% by weight based on the pack. The sheet-like pack is prepared by uniformly applying the pack on a substrate such as resin or metal, drying to form a sheet-like pack, peeling the sheet-like pack from the substrate, and cutting into a predetermined shape, thereby obtaining a product. Alternatively, a substrate such as nonwoven fabric made of polyester, nylon, polypropylene, acetate or the like, or the pack is applied on a film made of various resins and then the substrate is dried and cut into a predetermined shape, thereby obtaining a sheet-like pack which has been closely contacted and laminated on the substrate. The sheet-like pack is preferably dried so that the water content is within a range from 0.1 to 30% by weight in view of the form retention, pliability of the product as well as adhesion to the skin and quick-drying properties. The thickness of the sheet-like pack thus obtained is preferably within a range from 5 to 500 $\mu$m in view of the pliability of the product and applicability to the skin.

The pack of the present invention is used in the following manner. That is, the pack is applied to the skin and the pack is dried to form a film, and then the film is peeled off. The sheet-like pack of the present invention is used in the following manner. That is, water, beauty wash or the like is applied on the portion where the sheet-like pack is applied, and then the sheet-like pack is applied on the skin, dried and peeled off from the skin.

EXAMPLES

The present invention will be specifically described by way of Examples below. The sensory test of products was carried out in the following procedure.

(Sensory Test)

Using 20 female panelists, a sheet-like pack is applied on the position ranging from the bridge of the nose to the wings of the nose after washing the face and sufficiently wetting the nose with water. After drying over about 10 minutes, the sheet-like pack is peeled off. The respective evaluation items "remoisturizing properties (solubility)", "effect of removing stain of the skin", "degree of irritation or skin on peelings", "effect of firming up the skin" and "effect of moisturizing the skin" were evaluated by the number of persons who answered "Yes".

Examples 1 to 4 and Comparative Examples 1 to 3

Sheet-like Pack

Each of dispersions comprising the components shown in Table 1 is prepared and the dispersion is uniformly applied on a polypropylene nonwoven fabric (30 g/cm$^2$). Then, the dispersion is dried to prepare a sheet-like pack wherein a water content is 10% by weight and a pack portion has a thickness of about 200 $\mu$m. The surface of the resulting sheet-like pack of the present invention was covered with a release paper made of a polyester film treated with silicone to obtain a product. When using the product, the release paper was removed and the above sensory test was carried out. In the same manner as described above, except that the components shown in Table 2 were used, sheet-like packs of Comparative Examples were prepared. The amount of the Saxifrage extract is calculated on the basis of the dry residue. The component shown in Tables 1 to 2, PHYTELENE EGX-250 (trade name) manufactured by ICHIMARU PHARCOS co., LTD., is a mixed extract of IVY (Hederahelix), Clematis (Clematisvitalba), Seaweed, Horsetail (Equisetum arvense) and Meadosweet (Spiraed ulmaria).

With respect to the sheet-like packs of Examples 1 to 4 and Comparative Example 1 to 3, the above sensory test was carried out to obtain the evaluation results shown in the lower columns of Tables 1 to 2.

TABLE 1

| Components | | Example 1 | Example 2 | Example 3 | Example 4 |
|---|---|---|---|---|---|
| Polyacrylic acid | | 1.0 | 27.6 | 22.6 | 1.0 |
| Acrylic acid-methacrylic acid copolymer | | 35.0 | — | 30.0 | 35.0 |
| Polyvinyl alcohol | | 5.4 | 6.0 | — | 5.4 |
| Polyacrylamide | | — | — | 1.5 | — |
| Polyvinyl pyrrolidone | | 18.8 | — | — | 18.8 |
| Glycerin | | 4.2 | 4.2 | 4.2 | 4.2 |
| Titanium oxide | | 3.0 | 3.0 | 3.0 | 3.0 |
| Silica | | 5.0 | 5.0 | 5.0 | 5.0 |
| Methyl parahydroxy benzoate | | 0.02 | 0.02 | 0.02 | 0.02 |
| Saxifrage extract | | 0.3 | 0.3 | 0.3 | 0.3 |
| PHYTELENE EGX-250 | | 0.2 | 0.2 | 0.2 | 0.2 |
| Ethanol | | 2.4 | 2.4 | 2.4 | 2.4 |
| Perfume (menthol base) | | 0.5 | 0.5 | 0.5 | — |
| Purified water | | balance | balance | balance | balance |
| Evaluation results | Remoisturizing properties | 18 | 15 | 17 | 18 |
| | Removal of stain of skin | 14 | 19 | 14 | 14 |
| | No irritation | 17 | 18 | 15 | 17 |
| | Firm up of skin | 19 | 17 | 16 | 13 |
| | Moisturized feel of skin | 14 | 15 | 13 | 14 |

TABLE 2

| Components | | Comp. Example 1 | Comp. Example 2 | Comp. Example 3 |
|---|---|---|---|---|
| Polyacrylic acid | | — | 27.6 | 22.6 |
| Acrylic acid-methacrylic acid copolymer | | — | — | 30.0 |
| Polyvinyl alcohol | | 5.4 | 6.0 | - |
| Polyacrylamide | | — | — | 1.5 |
| Polyvinyl pyrrolidone | | 18.8 | — | — |
| Glycerin | | 4.2 | 4.2 | 4.2 |
| Titanium oxide | | 2.4 | 1.2 | 1.2 |
| Silica | | — | 1.2 | 1.2 |
| Methyl parahydroxy benzoate | | 0.02 | 0.02 | 0.02 |
| Perfume (menthol base) | | — | — | 0.5 |
| PHYTELENE EGX-250 | | 0.2 | 0.2 | 0.2 |
| Ethanol | | 2.4 | 2.4 | 2.4 |
| Purified water | | balance | balance | balance |
| Evaluation results | Remoisturizing properties | 10 | 14 | 16 |
| | Removal of stain of skin | 12 | 16 | 11 |
| | No irritation | 11 | 7 | 8 |
| | Firm up of skin | 9 | 9 | 10 |
| | Moisturized feel of skin | 10 | 9 | 10 |

INDUSTRIAL APPLICABILITY

As described above, the pack of the present invention allays irritation and pain on peeling, firms up the skin after use, moisturizes the skin, and has excellent remoisturizing properties, quick-drying properties and facility.

What is claimed is:

1. A pack comprising:
   a water-soluble polymer present in an amount of from 2.0 to 99.4% by total weight of the pack, wherein the water-soluble polymer includes at least one polymer selected from the group consisting of polyacrylic acid, polymethacrylic acid, and copolymers of acrylic acid and methacrylic acid;
   water present in an amount of from 0.1 to 30% by total weight of the pack;
   a perfume present in an amount of from 0.001 to 2.0% by total weight of the pack, wherein the perfume is selected from the group consisting of borneol and camphor; and
   a Saxifrage extract present in an amount of from 0.01 to 10.0% by weight calculated on the basis of the dry residue of the Saxifrage extract and the total weight of the pack,
   wherein the pack forms a pliable sheet that is laminated on a substrate selected from the group consisting of resin and nonwoven fabric, wherein a thickness of the pliable sheet is 5 to 500 μm.

2. A pack comprising:
   a water-soluble polymer and a Saxifrage extract dispersed or dissolved in a solvent, wherein the pack forms a peelable sheet when applied to human skin.

3. The pack according to claim 2, wherein said water-soluble polymer is at least one selected from the group consisting of polyacrylic acid, polymethacrylic acid, and copolymers of acrylic acid and methacrylic acid, said pack further comprising a perfume.

4. The pack according to claim 2, wherein the water-soluble polymer is present in an amount of from 1.0 to 80% by weight based on the total weight of the pack.

5. The pack according to claim 2, the Saxifrage extract is present in an amount of from 0.001 to 5.0% by weight calculated on the basis of the dry residue of the Saxifrage extract and the total weight of the pack.

6. The pack according to claim 2, the solvent is present in an amount of from 7 to 70% by weight based on the total weight of the pack.

7. The pack according to claim 4, wherein said water-soluble polymer is at least one selected from the group consisting of polyacrylic acid, polymethacrylic acid, and copolymers of acrylic acid and methacrylic acid, and said pack further including a perfume.

8. A pack comprising:
   a water-soluble polymer;
   a solvent present in an amount of from 0.1 to 30% by total weight of the pack; and
   a Saxifrage extract,
   wherein the pack forms a pliable sheet.

9. The pack according to claim 8, wherein the pliable sheet is laminated on a substrate selected from the group consisting of resin and nonwoven fabric.

10. The pack according to claim 8, wherein the solvent is water.

11. The pack according to claim 10, wherein the water-soluble polymer is present in an amount of from 2.0 to 99.4% by total weight of the pack.

12. The pack according to claim 10, the Saxifrage extract is present in an amount of from 0.01 to 10.0% by weight calculated on the basis of the dry residue of the Saxifrage extract and the total weight of the pack.

13. The pack according to any of claim 8, wherein a thickness of the pliable sheet is 5 to 500 μm.

14. The pack according to claim 4, wherein the pack farther comprises a perfume.

15. The pack according to claim 8, wherein the pack further comprises a perfume.

16. The pack according to claim 8, wherein said water-soluble polymer includes at least one polymer selected from the group consisting of polyacrylic acid, polymethacrylic acid, and copolymers of acrylic acid and methacrylic acid.

17. A method of using a pack comprising the steps of:
   remoisturizing a pack having a solvent present in an amount of from 0.1 to 30% by total weight of the pack and a Saxifrage extract;
   applying the pack to a portion of the human skin;
   drying the pack; and
   peeling the pack off the skin.

18. A method of using a pack comprising the steps of:
   apply the pack of any of claims 2–7 to a portion of the human skin;
   drying the pack;
   peeling the pack from the skin.

* * * * *